United States Patent [19]

Smith

[11] 4,050,455
[45] Sept. 27, 1977

[54] FOOT AND LEG BRACE
[75] Inventor: Lennie R. Smith, Kansas City, Kans.
[73] Assignee: The Raymond Lee Organization, Inc., New York, N.Y.
[21] Appl. No.: 708,511
[22] Filed: July 26, 1976
[51] Int. Cl.² .............................................. A61F 3/00
[52] U.S. Cl. .................... 128/80 F; 128/88
[58] Field of Search ............... 128/80 R, 80 F, 87 R, 128/88, 83

[56] References Cited

U.S. PATENT DOCUMENTS

| 4,255 | 11/1845 | Mills et al. | 128/88 |
|---|---|---|---|
| 385,507 | 7/1888 | DeCamp | 128/88 |
| 582,192 | 5/1897 | Entrekin | 128/88 |
| 932,177 | 8/1909 | Roth | 128/80 F |

Primary Examiner—John D. Yasko
Attorney, Agent, or Firm—Howard I. Podell

[57] ABSTRACT

A foot and leg brace assembly formed of three sections flexibly joined together. A first thigh section is a curved plate of a size to fit about the underside of a user's thigh, with the second leg section formed of a curved plate shaped to fit about the rear of the user's leg and the third foot section shaped to fit under the sole and behind the user's heel. All three sections are fitted with attachment straps, with the leg and thigh sections each fitted on their interior surfaces with a padding of foam rubber or plastic. A transverse bar is hinged to the rear of the sole of the foot section, and extends on both sides of the sole section, being held by a pair of opposed tension springs on an axis perpendicular to the axis of the foot section.

2 Claims, 3 Drawing Figures

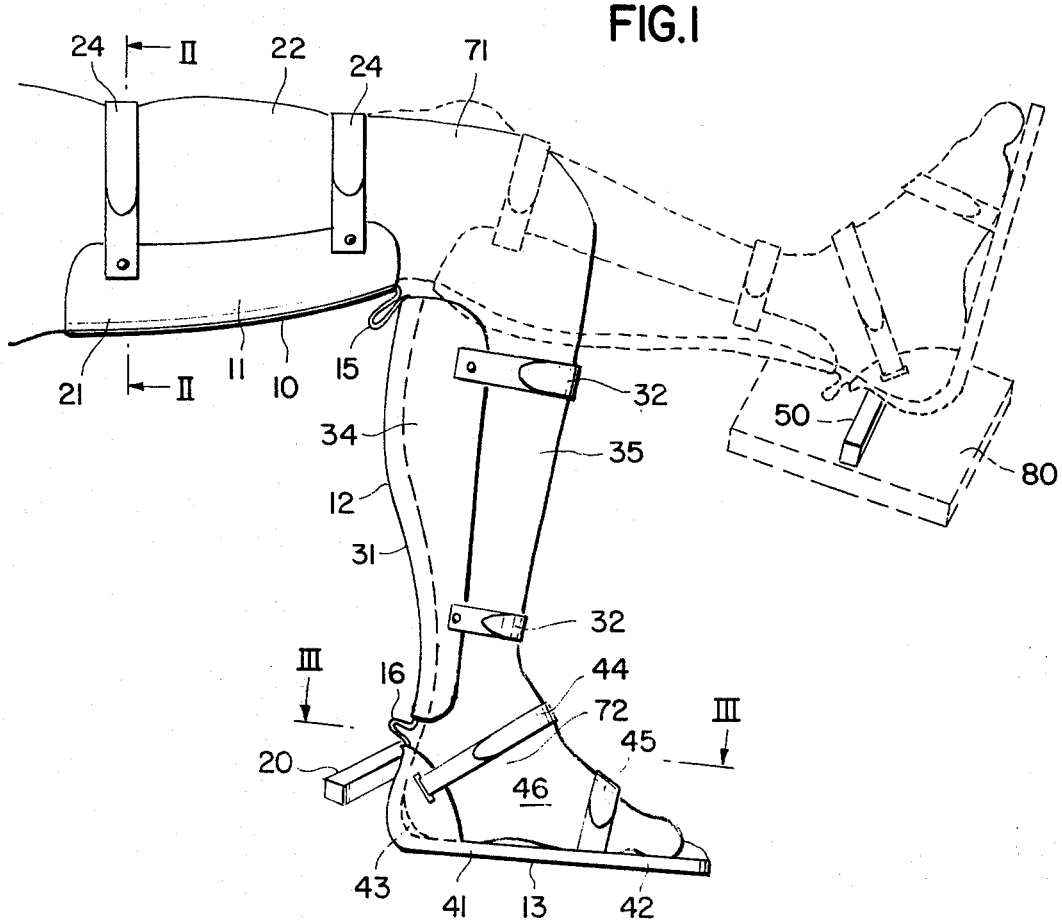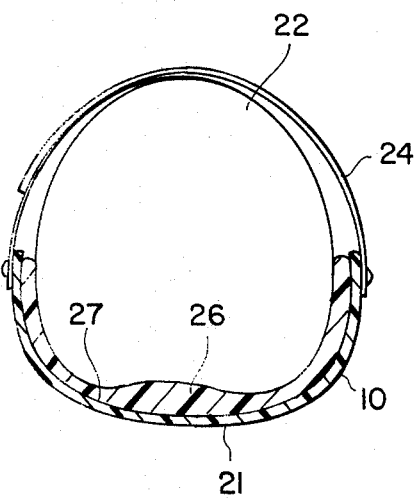

FOOT AND LEG BRACE

SUMMARY OF THE INVENTION

My invention is a foot and leg brace assembly formed of three sections flexibly joined together. A first thigh section is a curved plate of a size to fit about the underside of a user's thigh, with the second leg section formed of a curved plate shaped to fit about the rear of the user's leg and the third foot section shaped to fit under the sole and behind the user's heel. All three sections are fitted with attachment straps, with the leg and thigh sections each fitted on their interior surfaces with a padding of foam rubber or plastic. A transverse bar is hinged to the rear of the sole of the foot section, and extends on both sides of the sole section, being held by a pair of opposed tension springs on an axis perpendicular to the axis of the foot section.

BRIEF DESCRIPTION OF THE DRAWINGS:

The objects and features of the invention may be understood with reference to the following detailed description of an illustrative embodiment of the invention, taken together with the accompanying drawings in which:

FIG. 1 is a perspective view of the invention in use;

FIG. 2 is a sectional view of the thigh section, taken along line II—II of FIG. 1; and FIG. 3 is a sectional view of the foot section, taken along line III—III of FIG. 1.

DESCRIPTION OF THE PREFERRED EMBODIMENT

Turning now descriptively to the drawings, in which similar reference characters denote similar elements throughout the several views, FIGS. 1-3 illustrate the brace assembly 10 which is formed of a thigh section 11, joined by a flexible strap 15 to a leg section 12 that is joined by a flexible strap 16 to a foot section 13.

Thigh section 11 is formed of a curved plate 21 shaped to fit about the underside of a user's thigh 22 to which it may be fastened by attached straps 24. A sheet 26 of flexible padding, such as foam rubber or plastic is fixed to the undersurface 27 of plate 21.

Leg section 12 is similarly formed of a curved plate 31 fitted with straps 32 and shaped so as to fit about the sides and rear of the calf section 34 of a user's leg to which it is strapped. Padding is similarly attached to the undersurface of plate 31.

Foot section 13 is formed of a shaped plate 41 forming a flat sole section 42 fixed to a cupped heel section 43 and fitted with straps 44 fastened a heel section 43 and straps 45 fastened to sole section 42 for strapping to a user's foot 46.

A rigid bar 50 is pivotably mounted by pin 51 to a bracket 52 to the rear of heel section 43 so as to extend from each lateral side of heel section 42 in a plane parallel to the plane of sole section 42. A pair of opposed tension springs 56 each join an opposed end 57 of bar 50 to an external side 58 of heel section 43 so as to bias bar 50 along a transverse axis perpendicular to the longitudinal axis of sole section 42.

When strapped to the user, the three sections 11, 12 and 13 permit free movement of the knee joint 71 and heel joint 72 of a user, with bar 50 providing a rest, when extended to bear against a horizontal surface 80 for rotational exercise of the strapped leg of the user.

Since obvious changes may be made in the specific embodiment of the invention described herein, such modifications being within the spirit and scope of the invention claimed, it is indicated that all matter contained herein is intended as illustrative and not as limiting in scope.

Having thus described the invention, what I claim as new and desire to secure by Letters Patent of the United States is:

1. A brace assembly adaptable for fastening about the thigh, leg and foot of a user comprising a thigh section joined by a flexible strap to a leg section which is joined by a flexible strap to a foot section, each said section formed of a shaped plate, and each fitted with straps to fasten to the user, in which the thigh section plate is shaped to fit about the rear of a user's thigh and the leg section plate is shaped to fit about the rear of a user's leg, with foot section shaped of a flat section adaptable for fastening to the sole of a user and joined to a heel section of a shape to fit about the sides and rear of a user's heel, and in which a bar member is hinged to the exterior of the heel section to project laterally on each side of the heel section, together with tension spring means to bias the bar along an axis perpendicular to the longitudinal axis of the foot section.

2. A brace assembly adaptable for fastening about the leg and foot of a user comprising a leg section which is joined by a flexible strap to a foot section, each said section formed of a shaped plate, and each fitted with straps to fasten to the user, in which the leg section plate is shaped to fit about the rear of a user's leg, with the foot section shaped of a flat section adaptable for fastening to the sole of a user and joined to a heel section of a shape to fit about the sides and rear of a user's heal, and in which a bar member is hinged to the exterior of the heel section to project laterally on each side of the heel section, together with tension spring means to bias the bar along an axis perpendicular to the longitudinal axis of the foot section.

* * * * *